United States Patent
Yu et al.

(10) Patent No.: US 12,252,652 B2
(45) Date of Patent: Mar. 18, 2025

(54) METHYLPARAFFINS OBTAINED THROUGH ISOMERIZATION OF LINEAR OLEFINS AND USE THEREOF IN THERMAL MANAGEMENT

(71) Applicant: ExxonMobil Chemical Patents Inc., Baytown, TX (US)

(72) Inventors: Renyuan Yu, Humble, TX (US); Wenyih F. Lai, Bridgewater, NJ (US); Jorg F. W. Weber, Houston, TX (US); Anatoly I. Kramer, Baytown, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 110 days.

(21) Appl. No.: 17/756,831

(22) PCT Filed: Nov. 20, 2020

(86) PCT No.: PCT/US2020/061530
§ 371 (c)(1),
(2) Date: Jun. 3, 2022

(87) PCT Pub. No.: WO2021/113093
PCT Pub. Date: Jun. 10, 2021

(65) Prior Publication Data
US 2023/0066764 A1    Mar. 2, 2023

Related U.S. Application Data (60) Provisional application No. 62/944,456, filed on Dec. 6, 2019.

(30) Foreign Application Priority Data

Apr. 6, 2020  (EP) ..................................... 20168142

(51) Int. Cl.
*C10G 65/04* (2006.01)
*B01J 29/74* (2006.01)
(Continued)

(52) U.S. Cl.
CPC ........ *C10G 65/043* (2013.01); *B01J 29/7453* (2013.01); *B01J 29/7492* (2013.01);
(Continued)

(58) Field of Classification Search
CPC ............ C10G 65/043; C10G 2300/302; C10G 2300/304; C10G 2300/70; C10G 45/00;
(Continued)

(56) References Cited

U.S. PATENT DOCUMENTS

| 1,815,022 A | 7/1931 | Davis |
| 2,015,748 A | 10/1935 | Frolich |

(Continued)

FOREIGN PATENT DOCUMENTS

| CN | 208157582 U | 11/2018 |
| CN | 109841918 A | 6/2019 |

(Continued)

OTHER PUBLICATIONS

Extended European Search Report received for European Patent Application No. 20168142.6 mailed on Sep. 29, 2020, 9 Pages.
(Continued)

*Primary Examiner* — Ali Z Fadhel (57) ABSTRACT

Methylparaffins having limited methyl branching may be prepared by contacting at least one linear olefin with hydrogen in the presence of a dual-function supported catalyst comprising a solid acid component and a hydrogenation component under conditions sufficient to catalytically isomerize the at least one linear olefin into an intermediate product comprising one or more branched olefins, and hydrogenating the one or more branched olefins to form an
(Continued)

isoparaffin product comprising one or more methylparaffins. Heat transfer fluids comprising such methylparaffins may be used in various thermal management systems, such as within various systems of electric vehicles, server farms, or other locales in need of efficient heat transfer.

28 Claims, 3 Drawing Sheets (51) Int. Cl.
| | |
|---|---|
| B60L 58/26 | (2019.01) |
| C09K 5/10 | (2006.01) |
| H01M 10/613 | (2014.01) |
| H01M 10/625 | (2014.01) |
| H01M 10/6551 | (2014.01) |
| H01M 10/6567 | (2014.01) |

(52) U.S. Cl.
CPC ............... B60L 58/26 (2019.02); C09K 5/10 (2013.01); H01M 10/613 (2015.04); H01M 10/625 (2015.04); H01M 10/6551 (2015.04); H01M 10/6567 (2015.04); C10G 2300/302 (2013.01); C10G 2300/304 (2013.01); C10G 2300/70 (2013.01); H01M 2220/20 (2013.01)

(58) Field of Classification Search
CPC ..... C10G 45/64; B01J 29/743; B01J 29/7492; B60L 58/26; C09K 5/10; H01M 10/613; H01M 10/625; H01M 10/6551; H01M 10/6567; H01M 2220/20; Y02E 60/10; C07C 5/13
See application file for complete search history.

(56) References Cited

U.S. PATENT DOCUMENTS

| | | | |
|---|---|---|---|
| 2,191,498 A | 2/1940 | Reiff | |
| 2,387,501 A | 10/1945 | Dietrich | |
| 2,655,479 A | 10/1953 | Munday et al. | |
| 2,666,746 A | 1/1954 | Munday et al. | |
| 2,721,877 A | 10/1955 | Popkin et al. | |
| 2,721,878 A | 10/1955 | Popkin | |
| 3,197,405 A | 7/1965 | Suer | |
| 3,250,715 A | 5/1966 | Wyman | |
| 3,354,078 A | 11/1967 | Miale et al. | |
| 3,749,752 A * | 7/1973 | Pollitzer et al. | C07C 5/13 585/277 |
| 4,798,684 A | 1/1989 | Salomon | |
| 5,019,661 A * | 5/1991 | Mole | C07C 5/13 585/751 |
| 5,037,528 A * | 8/1991 | Garwood | C10G 65/043 208/18 |
| 5,084,197 A | 1/1992 | Galic et al. | |
| 5,135,638 A * | 8/1992 | Miller | B01J 29/7492 208/18 |
| 5,246,566 A * | 9/1993 | Miller | B01J 29/064 208/18 |
| 5,804,058 A * | 9/1998 | Grandvallet | C10G 45/64 208/111.1 |
| 6,080,301 A | 6/2000 | Berlowitz et al. | |
| 6,090,989 A | 7/2000 | Trewella et al. | |
| 6,165,949 A | 12/2000 | Berlowitz et al. | |
| 6,436,278 B1 * | 8/2002 | Benazzi | C10G 67/02 208/62 |
| 6,475,374 B1 * | 11/2002 | Leta | B01J 23/42 208/62 |
| 6,602,402 B1 * | 8/2003 | Benazzi | B01J 35/40 585/737 |
| 6,787,022 B1 * | 9/2004 | Berlowitz | C10G 65/043 208/18 |
| 7,125,818 B2 * | 10/2006 | Cody | B01J 29/064 502/79 |
| 7,220,350 B2 * | 5/2007 | Cody | C10G 45/60 208/89 |
| 7,482,300 B2 | 1/2009 | Lai et al. | |
| 7,704,930 B2 | 4/2010 | Deckman et al. | |
| 8,500,991 B2 | 8/2013 | Lai et al. | |
| 9,433,935 B2 | 9/2016 | Lai et al. | |
| 10,016,747 B2 | 7/2018 | Zhang et al. | |
| 2003/0150777 A1 * | 8/2003 | Johnson | C10G 65/043 208/950 |
| 2004/0065585 A1 * | 4/2004 | Benazzi | B01J 29/72 208/27 |
| 2004/0108246 A1 * | 6/2004 | Cody | B01J 29/068 208/89 |
| 2005/0006278 A1 * | 1/2005 | Miller | C10G 45/64 208/18 |
| 2005/0077209 A1 * | 4/2005 | Miller | C10M 171/02 208/27 |
| 2005/0133409 A1 * | 6/2005 | Abernathy | C10G 45/64 208/950 |
| 2005/0137435 A1 * | 6/2005 | Tiitta | C07C 5/2518 585/329 |
| 2005/0258078 A1 * | 11/2005 | Rosenbaum | C10G 2/32 208/950 |
| 2005/0261146 A1 * | 11/2005 | Rosenbaum | C10M 169/041 208/950 |
| 2006/0113216 A1 * | 6/2006 | Rosenbaum | C10M 177/00 585/6.6 |
| 2006/0199743 A1 * | 9/2006 | Rosenbaum | C10M 107/02 508/110 |
| 2006/0205610 A1 * | 9/2006 | Rosenbaum | C10G 2/32 208/18 |
| 2006/0207166 A1 * | 9/2006 | Herskowitz | C10G 3/49 44/385 |
| 2007/0010682 A1 * | 1/2007 | Myllyoja | C10G 45/02 554/174 |
| 2008/0156697 A1 * | 7/2008 | Dierickx | C10G 65/14 208/79 |
| 2010/0298616 A1 * | 11/2010 | Kettunen | C07C 9/22 585/277 |
| 2019/0264121 A1 | 8/2019 | China | |

FOREIGN PATENT DOCUMENTS

| | | |
|---|---|---|
| EP | 0686177 A1 | 12/1995 |
| EP | 2253608 A1 | 11/2010 |
| WO | 95/21225 A1 | 8/1995 |
| WO | 2019/082752 A1 | 5/2019 |
| WO | WO-2020222171 A1 * 11/2020 | ......... B01J 31/0278 |
| WO | 2021/113093 A1 | 6/2021 |

OTHER PUBLICATIONS

Miale, J. N. et al., (1966) "Catalysis by crystalline aluminosilicates: IV. Attainable catalytic cracking rate constants, and superactivity", Journal of Catalysis, vol. 6, No. 2, pp. 278-287.
Olson, D. H. et al., (1980) "Chemical and Physical Properties of the ZSM-5 Substitutional Series", Journal of Catalysis, vol. 61, No. 2, pp. 390-396.
International Search Report and Written Opinion received for PCT Application No. PCT/US2020/061530, mailed on Feb. 4, 2021, 12 Pages.
International Preliminary Report on Patentability received for PCT Application No. PCTUS2020061530, mailed on Jun. 16, 2022, 8 Pages.
Weisz, P.B. & Miale, J.N. (1965) "Superactive crystalline aluminosilicate hydrocarbon catalysts", Journal of Catalysis, vol. 4, p. 527-529.

* cited by examiner

METHYLPARAFFINS OBTAINED THROUGH ISOMERIZATION OF LINEAR OLEFINS AND USE THEREOF IN THERMAL MANAGEMENT

PRIORITY

This application is a National Phase Application claiming priority to PCT Application Serial No. PCT/US2020/061530 filed Nov. 20, 2020, which claims priority to and the benefit of U.S. Provisional Application No. 62/944,456, filed Dec. 6, 2019, and European Patent Application No. 20168142.6 which was filed Apr. 6, 2020, the disclosures of which are incorporated herein by reference in their entireties.

FIELD

The present disclosure relates to heat transfer fluids and methods for their production and use.

BACKGROUND

In the electric vehicle (EV) industry, numerous advances in battery technology have been made in recent years to promote greater power delivery and decreased charging frequency. Among the advancements needed to progress electric vehicle technology even further is the development of more effective cooling systems for promoting heat transfer from various electric vehicle components. Particular components of electric vehicles that may be in need of improved heat transfer include, for example, one or more batteries, axles, electric vehicle power electronics, and/or an electric motor. Rapid charging stations for electric vehicles may similarly be in need of efficient cooling. While certain components of an electric vehicle may be cooled to varying degrees using conventional jacketed cooling fluids and technology, such as aqueous glycol solutions also used in conjunction with internal combustion engines, effective cooling of the batteries and power components of an electric vehicle through direct cooling fluid contact represents an entirely different challenge due to the electrical conductivity of commonly used heat transfer fluids.

All batteries generate heat as they charge or discharge. The more rapid the rate of charge or discharge becomes, the greater the amount of heat generated per unit time. For small batteries, exposure to ambient atmosphere may effectively dissipate the discharged heat, such that separate cooling systems are not required. In electric vehicles, the large battery size and the rapid discharge rates needed to ensure satisfactory vehicle performance make heat dissipation much more of a concern. Likewise, rapid battery charging rates at electric vehicle recharging stations may also result in significant battery heating and present similar thermal management issues.

In addition to influencing or governing vehicle performance, battery temperatures outside a preferred operating range, typically from about 15° C. to 35° C. for lithium-ion batteries, may negatively impact the battery's performance. Internal temperature gradients between the various cells of a battery may similarly impact the battery's operational performance. In addition to poor battery or vehicle performance, operating a battery outside a preferred temperature range and/or with an internal thermal gradient may increase the risk for battery failure, runaway overheating, fire and/or explosion. Therefore, effective thermal management during battery charge or discharge and vehicle operation may become a limiting factor in how much the performance of electric vehicles may be further advanced. Other technologies in need of advanced thermal management may be similarly limited by existing heat transfer technologies.

Current strategies for cooling the batteries of electric vehicles may employ one or more of a phase change material, heat dissipation fins, or air cooling. Each of these approaches may have significant limitations, either in terms of the quantity of heat they are able to dissipate directly from the battery and/or due to their impact upon vehicle performance. Heat dissipation fins, for example, introduce excess weight that must be carried by the vehicle as it travels, thereby lowering the vehicle's efficiency and performance.

Cooling systems employing a heat transfer fluid are another heat dissipation strategy that may be employed for batteries and other heat-generating components of electric vehicles and other apparatuses or locales in need of effective thermal management. Since fluids may exhibit higher thermal conductivity and heat capacity values than does air, fluids may promote more effective heat dissipation from a battery or other heat-generating component, apparatus or locale than do other heat dissipation strategies. Moreover, a fluid may be placed in direct surface contact with a battery, power electronics, electric motor or other heat-generating component to promote optimal heat transfer, including configurations in which the heat-generating component is partially or fully immersed in the heat transfer fluid. Alternately, a suitable heat transfer fluid may be jacketed around and/or circulated through a heat-generating component, such as a battery, power electronics, or electric vehicle power component.

While immersion or partial immersion of a heat-generating component in a heat transfer fluid may afford optimal heat transfer, many heat transfer fluids presently in common use are unsuitable for immersion of batteries, power components, and/or electric motors therein due to electrical conductivity of the fluid. Aqueous heat transfer fluids, such as aqueous glycol solutions, for example, may be unsuitable for immersion of a battery, power component, or electric motor due to shorting and battery, component or motor failure that may occur when the electrically conductive heat transfer fluid contacts the battery's leads or various electrical components. Fluorocarbon fluids are insulators and may meet certain performance requirements for suitable heat transfer fluids, including satisfactory pour point values and flash point values, but fumes from burning of the fluids may lead to undesirable health and environmental effects. Silicone (polysiloxane) heat transfer fluids may be similarly problematic for cooling applications in electric vehicles and other apparatuses and locales in which effective thermal management is required.

Long-chain methylparaffins having limited methyl branching are insulators and may provide satisfactory heat transfer performance for applications in which aqueous glycol solutions may be unsuitable, but without the disadvantages associated with fluorocarbon, polysiloxane, and other alternative heat transfer fluids. However, efficient syntheses for long-chain methylparaffins having an acceptable combination of flash point, pour point, and kinematic viscosity have yet to be identified.

Limitations in heat transfer fluid technology are hindering further development of various fields in need of more effective thermal management, such as in electric vehicles and components therein, high-speed computers, server farms, data processing centers, cloud computing centers, cellular towers (particularly 5G), power stations, stationary battery storage locations, and others. More efficient syntheses for accessing alternative heat transfer fluids are needed to facilitate further advancement in these areas and others in which effective thermal management is needed.

SUMMARY

Methods for preparing methylparaffins may comprise contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins. Heat transfer fluids prepared by the foregoing methods are also disclosed herein.

Thermal management systems provided herein may comprise such heat transfer fluids, wherein the thermal management systems are configured to circulate the heat transfer fluid between a heat source and a heat dissipation structure. Battery systems provided herein may comprise such heat transfer fluids and a battery, in which the heat transfer fluid is in contact with the battery.

Thermal management methods of the present disclosure may comprise providing a heat transfer fluid comprising one or more methylparaffins, and operating or placing a heat-generating component in contact with the heat transfer fluid.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

DETAILED DESCRIPTION

The present disclosure relates to thermal management and, more specifically, to heat transfer fluids comprising methylparaffins and methods for preparing mixtures of methylparaffins.

As discussed above, effective thermal management can be challenging in a number of situations, particularly with respect to maintaining the batteries or other electrical components of electric vehicles in a desired operating temperature range while also preserving vehicle performance and maintaining high operational efficiency. Without effective thermal management, catastrophic battery and/or vehicle failure may occur. Effective cooling in other high-performance applications may be similarly problematic, particularly in instances where an apparatus or locale in need of cooling must remain electrically isolated from the heat transfer fluid. Heat transfer fluids based upon aqueous glycol solutions offer some of the best available thermal management performance to date, but the electrical conductivity of such fluids makes them unsuitable for certain applications, such as direct immersion of a battery, power component or electric motor therein. Indirect heat dissipation using such fluids or other thermal dissipation strategies may represent a much less effective thermal management solution, but they may be the only viable alternative when the only available heat transfer fluids with satisfactory performance are electrically conductive.

Methylparaffins having limited methyl branching, such as a single methyl group located upon a long carbon chain (e.g., 7-methylpentadecane), may have acceptable heat transfer properties for instances in which aqueous glycol solutions and other electrically conductive heat transfer fluids may not be satisfactory. Advantageously, such methylparaffins do not present the issues accompanying presently available insulating heat transfer fluids, such as fluorocarbons and polysiloxanes. Unfortunately, specific syntheses for such long-chain methylparaffins having a single methyl branch located deep within the carbon chain are not economically or technologically feasible at present, especially at commercially viable production scales. For example, hydrogenation of a vinylidene olefin, produced through metallocene-based dimerization of a linear alpha olefin, may afford a single methylparaffin, but technology to produce vinylidene olefins, and correspondingly the methylparaffins, are not advanced enough at present to facilitate economically feasible production at large scales. Alternative syntheses of methylparaffins through hydroisomerization of long-chain alkanes may result in a complex mixture of paraffinic products, often having a wide range of carbon chain lengths and multiple, random branching occurrences, thereby making the mixture unsuitable for many heat transfer applications. Excessive methyl branching of this type may render the methylparaffins too viscous for effective circulation in heat transfer applications. Pour points may also unacceptably increase when excessive methyl branching is present.

The present disclosure demonstrates that a mixture of isomeric methylparaffins, each residing within a narrow range of carbon chain length sizes and featuring limited methyl branching, may be a suitable alternative to heat transfer fluids containing a single long-chain methylparaffin. Advantageously, such mixtures of methylparaffins may be produced readily by applying the disclosure herein, in a considerably more straightforward manner than is presently feasible for producing a single methylparaffin compound. Such mixtures of methylparaffins may be formed in a single production line within a single reactor vessel using readily available, inexpensive linear olefins obtainable from the chemical and petrochemical industries. Both linear alpha olefins (LAOs) and linear internal olefins (LIOs) may undergo processing according to the disclosure herein to form methylparaffins having limited methyl branching, which may be suitable for use in various heat transfer applications.

More specifically, according to the disclosure herein, linear olefins may undergo ready isomerization in the presence of a dual-function supported catalyst comprising a solid acid component and a hydrogenation component that are located upon a common solid support. The solid acid component promotes formation of branched olefins having a range of methyl group and double bond positions, which may be subsequently hydrogenated under promotion of the hydrogenation component to remove the olefinic unsaturation and afford one or more methylparaffins each featuring a carbon chain at least one carbon atom shorter than the linear olefin from which it was produced. Methylparaffins produced in such a manner may feature predominantly one methyl group at any internal carbon atom (methylene group) of the carbon chain, wherein the methyl group results from isomerization of the carbon chain of the linear olefin. A very limited amount of more extensive isomerization and corresponding polymethylation may occur in some instances, such that one or more than one methyl group may be present upon some methylparaffin molecules. Alkylparaffins having alkyl groups larger than methyl are typically not formed in the methods described herein. As such, the linear olefins used to form methylparaffins according to the disclosure herein may be at least one carbon atom larger than the largest methylparaffin produced within a targeted size range. More typically, the linear olefins, such as LAOs or LIOs, are two or more carbon atoms larger than the largest methylparaffin within the targeted size range, including three, four, five, six, seven, eight, nine or ten carbon atoms larger, to account for a limited amount of carbon chain cracking that may occur in the presence of the solid acid component under the reaction conditions. The extent of cracking may be adjusted by modulating the reaction conditions and/or the solid acid component to afford different product distributions and/or different size ranges of methylparaffins from various linear olefin feeds. Moreover, a single linear olefin or a mixture of two or more linear olefins may be selected to target methylparaffins of a particular size range, which may produce targeted methylparaffin compositions in situ rather than through post-reaction blending. Varying the extent of cracking by modulating the reaction conditions and/or the solid acid component may allow linear olefins of varying carbon chain lengths to be used effectively in the disclosure herein. For example, when using LAOs to form methylparaffins according to the disclosure herein, the reaction conditions and/or solid acid component may be modulated to facilitate more effective utilization of long-chain LAOs that may otherwise be of limited value. Accordingly, the present disclosure herein offers considerable flexibility for producing a variety of methylparaffins having a range of carbon chain lengths from a range of linear olefin feedstocks. As a still further advantage, the reaction conditions and solid acid components used in the present disclosure do not lead to significant formation of heavy byproducts (i.e., reaction products having more carbon atoms do the one or more linear olefins) during olefin isomerization and hydrogenation due to the substantial absence of intramolecular reactions between the olefins or methylparaffins during this process.

Methylparaffins produced in accordance with the present disclosure may have a particularly desirable combination of viscosities, pour points, and flash points, among other physical properties, that may be suitable for affording good heat transfer properties and advantaged use thereof. In particular, methylparaffins having predominantly one methyl branch per $C_{14}$-$C_{16}$ carbon chain may feature flash points of about 100° C. or above, particularly about 130° C. or above, pour points of about −15° C. to about −95° C., particularly about −15° C. to about −50° C., and kinematic viscosity values of about 0.8 cSt to about 1.5 cSt at 100° C., particularly about 1.25 cSt to about 1.45 cSt at 100° C., which may represent particularly useful property ranges for heat transfer applications. Advantageously, these properties may be very comparable to those attainable with a single methylparaffin compound. The product distribution and/or the carbon chain length may also be further adjusted in the disclosure herein to afford additional tailoring of the flash point, pour point, viscosity and/or heat transfer efficiency in some cases. Other components may be combined with the methylparaffins of the present disclosure as well, as needed to modify any of the flash point, pour point, viscosity, heat transfer efficiency, or other performance property. Various application-specific needs may also dictate whether additional components need to be combined with the methylparaffins to facilitate use in a particular application.

Lithium-ion batteries currently used in electric vehicles and other applications have a practical operating temperature limit of about 70° C. to provide a generous safety factor below their failure temperature of about 125° C.-140° C., above which a runaway reaction leading to battery failure and a possible fire may occur. Certain methylparaffins produced in accordance with the disclosure herein may have a flash point of about 130° C. to about 150° C., including about 135° C. to about 145° C., or even a higher temperature, which should not be problematic in view of the much lower effective operating temperature of the battery. As such, minimal blending of the methylparaffins with other components may be needed to modify the flash point, particularly to raise the flash point, to produce effective heat transfer fluids for battery cooling. It is to be appreciated, however, that heat transfer fluids suitable for other applications may be formulated differently, and various application-specific additives may be combined with the methylparaffins in some cases. It is to be further appreciated that the flash point may be further increased, as needed or desired, for example, by increasing the proportion of heavier methylparaffins (e.g., $C_{16+}$ methylparaffins), which may be accomplished by appropriately choosing the LAO feedstock and/or catalyst used to produce the methylparaffins according to the disclosure herein.

All numerical values within the detailed description and the claims herein are modified by "about" or "approximately" with respect to the indicated value, and take into account experimental error and variations that would be expected by a person having ordinary skill in the art. Unless otherwise indicated, ambient temperature (room temperature) is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A," and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "Ce" refers to hydrocarbon(s) or a hydrocarbyl group having n carbon atom(s) per molecule or group, wherein n is a positive integer. Such hydrocarbon compounds may be one or more of linear, branched, cyclic, acyclic, saturated, unsaturated, aliphatic, or aromatic. Optional heteroatom substitution may be present in a hydrocarbon or hydrocarbyl group.

The terms "hydrocarbyl" and "hydrocarbyl group" are used interchangeably herein. The term "hydrocarbyl group"

refers to any $C_1$-$C_{100}$ hydrocarbon group bearing at least one unfilled valence position when removed from a parent compound.

The term "alkyl" refers to a hydrocarbyl group having no unsaturated carbon-carbon bonds. Optional heteroatom substitution or branching may be present in an alkyl group, unless otherwise specified herein.

The term "alkenyl" refers to a hydrocarbyl group having a carbon-carbon double bond. The terms "alkene" and "olefin" are used synonymously herein. Similarly, the terms "alkenic" and "olefinic" are used synonymously herein. Unless otherwise noted, all possible geometric isomers are encompassed by these terms.

The terms "linear" and "linear hydrocarbon" refer to a hydrocarbon or hydrocarbyl group having a continuous carbon chain without substantial side chain branches.

The term "linear alpha olefin (LAO)" refers to an alkenic hydrocarbon bearing a carbon-carbon double bond at a terminal (end) carbon atom of the main carbon chain. Most often, no side chain branches are present in a LAO, although there may occasionally be a minor amount of a branching component in a given LAO molecule. As such, the term "LAO" refers to eqivalently unbranched alkenic hydrocarbons and alkenic hydrocarbons bearing a single hydrocarbyl branch, particularly a methyl branch. In some embodiments, less than about 5 wt. % of methyl-branched LAOs may be present in a linear olefin feed.

The terms "branch," "branched" and "branched hydrocarbon" refer to a hydrocarbon or hydrocarbyl group having a linear main carbon chain in which a hydrocarbyl side chain extends from the linear main carbon chain. The term "unbranched" refers to a straight-chain hydrocarbon or hydrocarbyl group without side chain groups extending therefrom.

Accordingly, methylparaffins may be produced in accordance with the present disclosure by contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins.

Particular process configurations may include those in the linear olefin is a linear internal olefin (LIO), a linear alpha olefin (LAO), or any mixture thereof. LAOs may be particularly suitable due to their wide availability and more ready ability to undergo isomerization in accordance with the disclosure herein. To produce methylparaffins in a targeted size carbon chain size range of about 9 to about 25 carbon atoms, particularly a carbon chain size range of about 14 to about 16 carbon atoms, suitable LAOs may include 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, 1-heneicosene, 1-docosene, 1-tricosene, 1-tetracosene, 1-pentacosene, 1-hexacosene, 1-heptacosene, 1-octacosene, 1-nonacosene, 1-triacontene, or any mixture thereof, optionally in further combination with one or more LIOs. Linear olefins having a carbon backbone comprising about 10 to about 26 carbon atoms may be particularly desirable to produce methylparaffins in the foregoing carbon chain size range. In the disclosure herein, any single LAO or any mixture of two or more different LAOs may be used to produce methylparaffins having a targeted size range, optionally in further combination with one or more LIOs. LAOs suitable for use in the disclosure herein may be isolated from a petroleum refinery stream, or they may be synthesized by several processes starting from low molecular weight feedstock materials, such as via oligomerization of ethylene or through byproduct isolation from the Fischer-Tropsch synthesis. As such, LAOs represent a versatile and inexpensive feedstock for forming methylparaffins according to the disclosure herein, in addition to the process as a whole providing economic advantages over other routes for forming methylparaffins.

Methylparaffins produced in accordance with the present disclosure may include those in which at least a majority of the methylparaffins have one methyl branch, and each methylparaffin has a carbon backbone comprising about 9 to about 25 carbon atoms, or about 14 to about 25 carbon atoms. More extensive methylation may occur in some instances, such that the one or more methylparaffins collectively have a branching index ranging from 1 to about 3, including about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, or about 3.0, including any subrange thereof. In particular examples monomethylparaffins may predominate, such that the one or more methylparaffins may collectively have a branching index ranging from 1.0 to about 1.2, or 1.0 to about 1.4, or 1.0 to about 1.6, or 1.0 to about 1.8, or 1.0 to about 2.0. In still more particular examples, at least about 70 wt. % of the one or more methylparaffins may have a carbon backbone comprising about 14 atoms, 15 carbon atoms, 16 carbon atoms, 14 or 15 carbon atoms, 15 or 16 carbon atoms, or 14-16 carbon atoms, particularly instances in which such carbon backbones comprise one methyl group.

Branching index within a mixture of methylparaffins may be calculated as follows: (0×% linear paraffins+1×% monobranched paraffins+2×% di-branched paraffins 3×% tri-branched paraffins)/100; where % linear+% monobranched+% di-branched+% tri-branched=100%. More highly branched methylparaffins (e.g., tetra-branched and higher) may be weighted similarly to determine the branch index. For example, a mixture of $C_{16}$ methylparaffins composed of 10% linear $C_{16}$, 30% monobranched $C_{16}$, 50% di-branched $C_{16}$, and 10% tri-branched $C_{16}$ has a branching index of 1.6.

Scheme 1 below illustrates the general process whereby a linear alpha olefin (e.g., a $C_{16+}$ and/or $C_{18+}$ LAO) may be converted into methylparaffins in the presence of a dual-function supported catalyst comprising a solid acid component and a hydrogenation component. As shown, the solid acid component may first isomerize the LAO into a monobranched internal olefin, in which the one methyl group resulting from isomerization may 'walk' down the carbon chain to any available methylene group to form one or more branched olefins (Structures 1A and 1B, which may be formed in any proportion). In Scheme 1, variable m is an integer representing the number of methylene groups in the linear alpha olefin undergoing isomerization. Variables o and n are each integers that may range from 0 up to one less than m, and the sum of o+n is m−1. Although not shown in Scheme 1, the double bond may also migrate to additional positions beyond the terminal carbon atom. The position of the double bond becomes moot once the branched olefins undergo hydrogenation to form the corresponding methylparaffins (Structures 2A and 2B) according to the disclosure herein. A similar range of structures may be produced starting from LIOs as well. Thus, methylparaffins produced in accordance with the disclosure herein, may feature the methyl group residing at any of C-2, C-3, C-4, and so on. It is to be appreciated that the position and distribution of the resulting methyl groups in the resulting one or more methylparaffins may depend upon the solid acid component used, the reaction conditions, the time over which the isomerization reaction is allowed to equilibrate, and any combination thereof. Although not shown in Scheme 1, a limited amount of further isomerization may occur upon some of the molecules to result in some of the methylparaffins having more than one methyl group.

Scheme 1

No cracking is depicted in Scheme 1. It is to be appreciated that methylparaffins formed from LAOs or LIOs under cracking conditions may have their carbon chains shortened by one or more additional carbon atoms, in addition to the carbon chain shortening that results from isomerization. Scheme 2 below illustrates the general process whereby a linear alpha olefin (e.g., a $C_{18+}$ LAO) may be converted into methylparaffins in the presence of a dual-function supported catalyst comprising a solid acid component and a hydrogenation component under cracking conditions, wherein p is the number of carbon atoms lost during cracking and is an integer of 2 or greater. Variable m is again an integer representing the number of methylene groups in the linear alpha olefin. Variables o' and n' are integers ranging from 0 to m–p, and the sum of o'+n' is m–p. Mixtures of methylparaffins formed with and without cracking occurring may be formed in the disclosure herein.

Scheme 2

Suitable hydrogenation components and solid acid components are provided in U.S. Pat. Nos. 7,482,300; 9,433,935, and 10,016,747, each of which is incorporated herein by reference in its entirety. Further description of suitable hydrogenation components, solid acid components, and reaction conditions follows below.

Suitable hydrogenation conditions, hydrogenation components suitable to promote hydrogenation, reactors and the like will be familiar to one having ordinary skill in the art. Suitable hydrogenation components may comprise a metal capable of activating molecular hydrogen from Groups 6-12 of the Periodic Table, particularly Groups 6 and 8-10. Examples of suitable metals for promoting hydrogenation include Ni, Mo, Co, W, Mn, Cu, Zn, Ru, Pt and Pd, particularly Ni, Pt or Pd. Mixtures of these metals may also be used to promote hydrogenation in the disclosure herein, such as Co/Mo, Ni/Mo, Ni/W and Pt/Pd. The amount of hydrogenation component may range from about 0.1 wt. % to about 30 wt. % per unit weight of die linear olefin undergoing isomerization, such as at least about 0.1 wt. %, or at least about 0.3 wt. %, or at least about 0.5 wt. %, or at least about 0.75. wt. %, or at least about 1.0 wt. %, or at least about 1.5 wt. %, or at least about 2 wt. %, or at least about 5 wt. %. Additionally or alternately, the amount of hydrogenation catalyst may be a non-zero amount less than about 30 wt. %, such as a non-zero amount less than about 20 wt. %, or a non-zero amount less than about 15 wt. %, or a non-zero amount less than about 10 wt. %, or a non-zero amount less than about 5 wt. %, or a non-zero amount less than about 2 wt. %.

Suitable solid acid components may include zeolites, particularly those containing 10- or 12-membered rings in the zeolite structural framework. Particularly suitable zeolites may include ZSM-48 and ZSM-23, as well as several others. Other suitable zeolite solid acid components may include, for example, ZSM-5, ZSM-11, ZSM-12, ZSM-22, ZSM-35, zeolite Beta, TON (Theta-1), or a combination thereof, for example ZSM-23 and/or ZSM-48, optionally in further combination with one or more of the foregoing zeolites. Other examples of solid acid components that may be suitable for use in the disclosure herein include, for example, EU-1, ZSM-35 (or ferrierite), ZSM-11, ZSM-57, NU-87, SAPO-11, ZSM-22, EU-2, EL-11, ZBM-30 and isostructural materials such as NU-10, EU-13, KZ-1, and NU-23. These solid acid components may similarly be used in combination with ZSM-48, ZSM-23, or other zeolite materials.

The solid acid component and the hydrogenation component may be concurrently supported in the disclosure herein. Suitable supported catalyst configurations include those in which the hydrogenation component is deposited upon the solid acid component or both the solid acid component and the hydrogenation component are disposed on a common solid support or binder in the disclosure herein. Suitable solid supports and binders are generally inert toward promoting isomerization and/or cracking and may include substances such as, for example, alumina, titania, silica, silica-alumina, zirconia, or a combination thereof, for example alumina and/or titania or silica and/or zirconia and/or titania. A loading of the hydrogenation component relative to the solid acid component in the dual-function catalyst may range from about 0.01 wt. % to about 20 wt. %, or about 0.05 wt. % to about 15 wt. %, or about 0.1 wt. % to about 2 wt. %, or about 0.1 wt. % to about 1 wt. %.

Particular examples of temperatures sufficient to catalytically isomerize linear olefins into one or more branched olefins may include a temperature of about 200° C. to about 300° C., or about 200° C. to about 220° C., or about 220° C. to about 240° C., or about 240° C. to about 260° C., or about 260° C. to about 280° C., or about 280° C. to about 300° C.

Total pressures used when forming methylparaffins according to the disclosure herein may range from about 50 psig to about 500 psig, or about 100 psig to about 200 psig, or about 200 psig to about 300 psig.

Hydrogen may be present at a flow rate sufficient to promote hydrogenation of the initially isomerized reaction product. In particular instances, the flow rate may be such that hydrogen is present in a molar amount of about 7:1 to about 70:1 with respect to the linear olefins undergoing isomerization.

Linear hourly space velocity (LHSV) values when forming methylparaffins according to the disclosure herein may include, for example, about 1 h$^{-1}$ to about 5 h$^{-1}$, or about 1 h$^{-1}$ to about 2 h$^{-1}$, or about 2 h$^{-1}$ to about 3 h$^{-1}$, or about 3 h$^{-1}$ to about 4 W, or about 4 h$^{-1}$ to about 5 h$^{-1}$.

Methylparaffins having carbon chain size range of about 9 to about 25 carbon atoms may collectively have a flash point (ASTM D92) of about 90° C. or higher, such as about 90° C. to about 300° C., and/or have a pour point (ASTM D97) of about −15° C. or lower, such as about −15° C. to about −98° C. or about −40° C. to about −98° C., and/or a kinematic viscosity (ASTM D445) at 100° C. of about 2.5 cSt or lower, such as about 0.5 cSt to about 2.5 cSt.

Certain methylparaffins formed in accordance with the disclosure herein may comprise those in which at least about 70% of the methylparaffins comprise a carbon backbone having 14 to 16 carbon atoms. Such methylparaffins may afford particularly advantageous heat transfer properties. Such methylparaffins may collectively have a flash point (ASTM D92) of about 130° C. or higher, or about 135° C. or higher or about 140° C. or higher, including about 135° C. to about 145° C. or about 130° C. to about 150° C., and/or have a pour point (ASTM D97) of about −15° C. to about −50° C., or about −30° C. to about −50° C., or about −40° C. to about −50° C., and/or have a kinematic viscosity (ASTM D445) at 100° C. of about 1.5 cSt or less, including about 1.25 cSt to about 1.45 cSt. The term "collectively" means "in combination" herein. Thus, a plurality of methylparaffins formed according to the disclosure herein may collectively exhibit one or more of the foregoing properties, even if some of the methylparaffins within a mixture of methylparaffins do not individually exhibit a value within the desired range.

Additional components may be included in combination with the methylparaffins disclosed herein. Among the additional components that may be present in combination with the methylparaffins to address particular application-specific needs include, for example, base oils, aromatic hydrocarbons, polyalphaolefins, paraffins, esters, ethers, gas-to-liquids base oils, Fischer-Tropsch wax-derived base oils, wax-derived hydroisomerized base oils, silicone oils, antioxidants, corrosion inhibitors, antifoam agents, antiwear agents, dispersants, detergents, viscosity modifiers, and any combination thereof. Suitable examples of additional components that may be present are discussed hereinafter.

A wide range of base oils suitable for inclusion in heat transfer fluids is known in the art. Base oils that may be useful in the present disclosure include natural oils, mineral oils and synthetic oils, and unconventional oils (or mixtures thereof), any of which can be used unrefined, refined, or rerefined, the latter being also known as reclaimed or reprocessed oil. Unrefined oils include those obtained directly from a natural or synthetic source and used without added purification. These include shale oil obtained directly from retorting operations, petroleum oil obtained directly from primary distillation, and ester oil obtained directly from an esterification process. Refined oils are similar to the oils discussed for unrefined oils except refined oils are subjected to one or more purification steps to improve at least one heat transfer fluid base oil property. One skilled in the art will be familiar with many purification processes. Such purification processes may include solvent extraction, secondary distillation, acid extraction, base extraction, filtration, percolation, and any combination thereof. Rerefined oils are obtained by processes analogous to refined oils but using an oil that has been previously used as a feed stock.

Groups I, II, III, IV and V are broad base oil stock categories developed and defined by the American Petroleum Institute (API Publication 1509; www.API.org) to create guidelines for heat transfer fluid base oils. Group I base stocks have a viscosity index of between about 80 to 120 and contain greater than about 0.03% sulfur and/or less than about 90% saturates. Group II base stocks have a viscosity index of between about 80 to 120, and contain less than or equal to about 0.03% sulfur and greater than or equal to about 90% saturates. Group III base stocks have a viscosity index greater than about 120 and contain less than or equal to about 0.03% sulfur and greater than about 90% saturates. Group IV base stocks includes polyalphaolefins (PAOs). Group V base stocks includes base stocks not included in Groups I-IV. Table 1 below summarizes properties of each of these five groups.

TABLE 1

| | Base Oil Properties | | |
|---|---|---|---|
| | Saturates | Sulfur | Viscosity Index |
| Group I | <90 and/or | >0.03% and | ≥80 and <120 |
| Group II | ≥90 and | ≤0.03% and | ≥80 and <120 |
| Group III | ≥90 and | ≤0.03% and | ≥120 |
| Group IV | polyalphaolefins (PAOs) | | |
| Group V | All other base oil stocks not included in Groups I, II, III or IV | | |

Natural oils include animal oils, vegetable oils (castor oil and lard oil, for example), and mineral oils. Animal and vegetable oils possessing favorable thermal oxidative stability can be used. Of the natural oils, mineral oils are preferred. Mineral oils vary widely as to their crude source, for example, as to whether they are paraffinic, naphthenic, or mixed paraffinic-naphthenic. Oils derived from coal or shale may also be useful. Natural oils also may vary as to the method used for their production and purification, for example, their distillation range and whether they are straight run or cracked, hydrorefined, or solvent extracted.

Group II and/or Group III hydroprocessed or hydrocracked base stocks, including synthetic oils such as alkyl aromatics and synthetic esters are also well known base stock oils that may be used in the disclosure herein.

Synthetic oils include hydrocarbon oil. Hydrocarbon oils include oils such as polymerized and interpolymerized olefins (polybutylenes, polypropylenes, propylene isobutylene copolymers, ethylene-olefin copolymers, and ethylene-alphaolefin copolymers, for example). Polyalphaolefin (PAO) oil base stocks are commonly used synthetic hydrocarbon oil. By way of example, PAOs derived from $C_8$, $C_{10}$, $C_{12}$, or $C_{14}$ olefins or mixtures thereof may be utilized, as described in U.S. Pat. Nos. 4,956,122; 4,827,064; and 4,827,073, each of which is incorporated herein by reference.

Other useful oil base stocks include wax isomerate base stocks and base oils, comprising hydroisomerized waxy stocks (e.g., waxy stocks such as gas oils, slack waxes, fuels hydrocracker bottoms, and the like), hydroisomerized Fischer-Tropsch waxes, gas-to-liquids (GTL) base stocks and base oils, and other wax isomerate hydroisomerized base stocks and base oils, or mixtures thereof. Fischer-Tropsch waxes, the high boiling point residues of a Fischer-Tropsch synthesis, are highly paraffinic hydrocarbons with very low sulfur content. The hydroprocessing used for the production of such base stocks may use an amorphous hydrocracking/hydroisomerization catalyst, such as one of the specialized lube hydrocracking (LHDC) catalysts or a crystalline hydrocracking/hydroisomerization catalyst, preferably a zeolitic catalyst.

Gas-to-liquids (GTL) base oils, Fischer-Tropsch wax-derived base oils, and other wax-derived hydroisomerized (wax isomerate) base oils may be advantageously used in the present disclosure, and may have useful kinematic viscosities at 100° C. of about 3 cSt to about 50 cSt, preferably about 3 cSt to about 30 cSt, more preferably about 3.5 cSt to about 25 cSt, as exemplified by GTL 4 with kinematic viscosity of about 4.0 cSt at 100° C. and a viscosity index of about 141. These gas-to-liquids (GTL) base oils, Fischer-Tropsch wax-derived base oils, and other wax-derived hydroisomerized base oils may have useful pour points of about −20° C. or lower, and under some conditions may have advantageous pour points of about −25° C. or lower, with useful pour points of about −30° C. to about −40° C. or lower. Useful compositions of gas-to-liquids (GTL) base oils, Fischer-Tropsch wax-derived base oils, and wax-derived hydroisomerized base oils are recited in U.S. Pat. Nos. 6,080,301; 6,090,989; and 6,165,949, for example, and are incorporated herein in their entirety by reference.

Esters may comprise a useful base stock. Additive solvency and seal compatibility characteristics may be secured by the use of esters such as the esters of dibasic acids with monoalkanols and the polyol esters of monocarboxylic acids. Esters of the former type include, for example, the esters of dicarboxylic acids such as phthalic acid, succinic acid, alkyl succinic acid, alkenyl succinic acid, maleic acid, azelaic acid, suberic acid, sebacic acid, fumaric acid, adipic acid, linoleic acid dimer, malonic acid, alkyl malonic acid, alkenyl malonic acid, and the like, with a variety of alcohols such as butyl alcohol, hexyl alcohol, dodecyl alcohol, 2-ethylhexyl alcohol, and the like. Specific examples of these types of esters include dibutyl adipate, di-(2-ethylhexyl) sebacate, di-n-hexyl fumarate, dioctyl sebacate, diisooctyl azelate, diisodecyl azelate, dioctyl phthalate, didecyl phthalate, dieicosyl sebacate, and the like.

Base oils useful in the present disclosure may include any of the variety of oils corresponding to API Group I, Group II, Group III, Group IV, and Group V oils, and mixtures thereof, preferably API Group II, Group III, Group IV, and Group V oils, and mixtures thereof, more preferably Group III, Group IV, and Group V base oils, and mixtures thereof. Highly paraffinic base oils can be used to advantage in heat transfer fluids useful in the present disclosure. Minor quantities of Group I base stock, such as the amount used to dilute additives for blending into formulated lube oil products, can also be used. Even in regard to the Group II stocks, it is preferred that the Group II stock be in the higher quality range associated with that stock, such as a Group II base stock having a viscosity index in the range 100<VI<120.

The base oil may constitute a major or minor component of heat transfer fluids of the present disclosure and may be present in an amount ranging from about 50 to about 99 wt. %, including from about 70 to about 95 wt. % or from about 85 to about 95 wt. %, based on the total weight of the composition. The base oil conveniently has a kinematic viscosity, according to ASTM standards, of about 2.5 cSt to about 12 cSt (or mm$^2$/s) at 100° C. and preferably of about 2.5 cSt to about 9 cSt (or mm$^2$/s) at 100° C. Mixtures of synthetic and natural base oils may be used if desired. Bi-modal mixtures of Group I, II, III, IV, and/or V base stocks may be used, if desired.

The heat transfer fluids containing methylparaffins of the present disclosure may additionally contain one or more commonly used heat transfer fluid performance additives including but not limited to antioxidants, corrosion inhibitors, antifoam agents, and others. These additives are commonly delivered with varying amounts of diluent oil, which may range from 5 wt. % to 50 wt. % of the heat transfer fluid. The additives useful in this disclosure do not have to be soluble in the heat transfer fluids. The types and quantities of performance additives used in the heat transfer fluids of the present disclosure are not limited by the examples shown herein as illustrations.

The heat transfer fluids may include at least one antioxidant. Antioxidants retard the oxidative degradation of fluids during service. Such degradation may result in deposits on metal surfaces, the presence of sludge, or a viscosity increase in the heat transfer fluid. One having ordinary skill in the art will appreciate that a wide variety of oxidation inhibitors may be useful in heat transfer fluids. See, Klamann in Lubricants and Related Products, Verlag Chemie, Deerfield Beach, FL; ISBN 0-89573-177-0, and U.S. Pat. Nos. 4,798,684 and 5,084,197, for example.

The heat transfer fluids may include at least one corrosion inhibitor. Corrosion inhibitors are used to reduce the degradation of metallic parts that are in contact with the heat transfer fluids. Corrosion inhibitors are additives that protect metal surfaces against chemical attack by water or other contaminants. A wide variety of corrosion inhibitors are commercially available. As used herein, corrosion inhibitors include antirust additives and metal deactivators. Suitable corrosion inhibitors also include aryl thiazines, alkyl substituted dimercaptothiodiazoles, alkyl substituted dimercaptothiadiazoles, and mixtures thereof.

One type of a suitable corrosion inhibitor is a polar compound that wets the metal surface preferentially, protecting it with a film of oil. Another type of corrosion inhibitor absorbs water by incorporating it in a water-in-oil emulsion so that only the oil touches the metal surface. Yet another type of corrosion inhibitor chemically adheres to the metal to produce a non-reactive surface. Examples of suitable additives include zinc dithiophosphates, metal phenolates, basic metal sulfonates, fatty acids and amines. Such additives may be used in an amount of about 0.01 wt. % to 5 wt. %, preferably about 0.01 to 1.5 wt. %, more preferably 0.01 to 0.2 wt. %, still more preferably 0.01 to 0.1 wt. % (on an as-received basis) based on the total weight of the heat transfer fluid.

Antifoam agents may advantageously be added to heat transfer fluids. These agents retard the formation of stable foams. Silicones and organic polymers are typical antifoam agents. For example, polysiloxanes, such as silicone oil or polydimethylsiloxane, provide antifoam properties. Antifoam agents are commercially available and may be used in conventional minor amounts along with other additives such as demulsifiers; usually the amount of these additives combined is less than 1 wt. % and often less than 0.1 wt. %. In an embodiment, such additives may be used in an amount of about 0.01 to 5 wt. %, including 0.1 to 3 wt. % or about 0.5 to 1.5 wt. %.

The heat transfer fluids may include at least one antiwear agent. Examples of suitable antiwear agents include oil soluble amine salts of phosphorus compounds, sulphurized olefins, metal dihydrocarbyldithio-phosphates (such as zinc dialkyldithiophosphates), thiocarbamate-containing compounds, such as thiocarbamate esters, thiocarbamate amides, thiocarbamic ethers, alkylene-coupled thiocarbamates, and bis(S-alkyldithiocarbamyl) disulphides.

Antiwear agents used in the heat transfer fluids may be ashless or ash-forming in nature. Preferably, the antiwear agent is ashless. So-called ashless antiwear agents are materials that form substantially no ash upon combustion. For example, non-metal-containing antiwear agents are considered ashless.

The heat transfer fluids of the present disclosure may additionally contain one or more of the other commonly used heat transfer fluid performance additives including but not limited to dispersants, detergents, viscosity modifiers, metal passivators, ionic liquids, extreme pressure additives, anti-seizure agents, wax modifiers, fluid-loss additives, seal compatibility agents, lubricity agents, anti-staining agents, chromophoric agents, defoamants, demulsifiers, emulsifiers, densifiers, wetting agents, gelling agents, tackiness agents, colorants, and others. For a review of many commonly used additives, see Klamann in Lubricants and Related Products, Verlag Chemie, Deerfield Beach, FL; ISBN 0-89573-177-0; see also U.S. Pat. No. 7,704,930, the disclosure of which is incorporated herein by reference in its entirety. These additives are commonly delivered with varying amounts of diluent oil, which may range from 5 wt. % to 50 wt. %.

The heat transfer fluids may include at least one dispersant. During electrical apparatus component operation, oil-insoluble oxidation byproducts are produced. Dispersants help keep these byproducts in solution, thus diminishing their deposition on metal surfaces. Dispersants used in the formulation of the heat transfer fluids may be ashless or ash-forming in nature. Preferably, the dispersant is ashless. So called ashless dispersants are organic materials that form substantially no ash upon combustion. For example, non-metal-containing or borated metal-free dispersants are considered ashless.

Suitable dispersants typically contain a polar group attached to a relatively high molecular weight hydrocarbon chain. The polar group typically contains at least one element of nitrogen, oxygen, or phosphorus. Typical hydrocarbon chains contain 50 to 400 carbon atoms.

The heat transfer fluids may include at least one detergent. Illustrative detergents useful in this disclosure include, for example, alkali metal detergents, alkaline earth metal detergents, or mixtures of one or more alkali metal detergents and one or more alkaline earth metal detergents. A typical detergent is an anionic material that contains a long chain hydrophobic portion of the molecule and a smaller anionic or oleophobic hydrophilic portion of the molecule. The anionic portion of the detergent is typically derived from an organic acid such as a sulfur acid, carboxylic acid (e.g., salicylic acid), phosphorous acid, phenol, or mixtures thereof. The counterion is typically an alkaline earth or alkali metal.

Viscosity modifiers (also known as viscosity index improvers (VI improvers), and viscosity improvers) can be included in the heat transfer fluids of this disclosure. Viscosity modifiers provide heat transfer fluids with high and low temperature operability. These additives impart shear stability at elevated temperatures and acceptable viscosity at low temperatures. Suitable viscosity modifiers include high molecular weight hydrocarbons, polyesters and viscosity modifier dispersants that function as both a viscosity modifier and a dispersant. Typical molecular weights of these polymers are about 10,000 to 1,500,000, more typically about 20,000 to 1,200,000, and even more typically between about 50,000 to 1,000,000.

Examples of suitable viscosity modifiers include linear or star-shaped polymers and copolymers of methacrylate, butadiene, olefins, or alkylated styrenes. Polyisobutylene is a commonly used viscosity modifier. Another suitable viscosity modifier is polymethacrylate (copolymers of various chain length alkyl methacrylates, for example), some formulations of which also serve as pour point depressants. Other suitable viscosity modifiers include copolymers of ethylene and propylene, hydrogenated block copolymers of styrene and isoprene, and polyacrylates (copolymers of various chain length acrylates, for example). Specific examples include styrene-isoprene or styrene-butadiene based polymers of 50,000 to 200,000 molecular weight.

The heat transfer fluids may include at least one metal passivator. The metal passivators/deactivators include, for example, benzotriazole, tolyltriazole, 2-mercaptobenzothiazole, dialkyl-2,5-dimercapto-1,3,4-thiadiazole; N,N'-disalicylideneethylenediamine, N,N'-disalicylidenepropylenediamine; zinc dialkyldithiophosphates and dialkyl dithiocarbamates. The metal passivator concentration in the heat transfer fluids of this disclosure can range from about 0.01 to about 5.0 wt. %, including about 0.01 to about 3.0 wt. % or about 0.01 wt. % to about 1.5 wt. %, based on the total weight of the heat transfer fluid.

Ionic liquids are so-called salt melts, which are preferably liquid at room temperature and/or by definition have a melting point less than 100° C. They have almost no vapor pressure and therefore have no cavitation properties. In addition, through the choice of the cations and anions in the ionic liquids, the lifetime of the heat transfer fluid may be increased, and by adjusting the electric conductivity, these liquids can be used in equipment in which there is an electric charge buildup, such as electric vehicle components. Suitable cations for ionic liquids include a quaternary ammonium cation, a phosphonium cation, an imidazolium cation, a pyridinium cation, a pyrazolium cation, an oxazolium cation, a pyrrolidinium cation, a piperidinium cation, a thiazolium cation, a guanidinium cation, a morpholinium cation, a trialkylsulfonium cation or a triazolium cation.

In electrical apparatus components, static electricity is generated, especially when the heat transfer fluid is in use. To reduce that hazard, a conductive antistatic additive can be added to and distributed throughout the heat transfer fluids. The heat transfer fluid will thereby avoid reduction in its performance associated with local breakdown of the base stock and safety problems from static electric build-up.

A class of products called "antistatic fluids" or "antistatic additives," which also are petroleum distillates, can be added to adjust the conductivity of heat transfer fluids to safe levels, such as at or above 100 pico-siemens per meter conductivity. Very small quantities of these antistatic fluids are required to raise the conductivity to the desired levels, such as 10 to 30 milliliters per 1,000 gallons of hydrocarbon.

Conventional pour point depressants (also known as lube oil flow improvers) may be added to the heat transfer fluids of the present disclosure. Pour point depressants may be added to heat transfer fluids of the present disclosure to lower the minimum temperature at which the fluid will flow or can be poured. Examples of suitable pour point depressants include polymethacrylates, polyacrylates, polyarylamides, condensation products of haloparaffin waxes and aromatic compounds, vinyl carboxylate polymers, and terpolymers of dialkylfumarates, vinyl esters of fatty acids and allyl vinyl ethers. U.S. Pat. Nos. 1,815,022; 2,015,748; 2,191,498; 2,387,501; 2,655,479; 2,666,746; 2,721,877; 2,721,878; and 3,250,715, each of which is incorporated herein by reference, describe useful pour point depressants and/or the preparation thereof. Such additives may be used in an amount of about 0.01 to 5 wt. %, preferably about 0.1 to 3 wt. %, and more preferably about 0.5 to 1.5 wt. %.

The heat transfer fluids can include at least one seal compatibility agent. Seal compatibility agents help to swell elastomeric seals by causing a chemical reaction in the fluid or physical change in the elastomer. Suitable seal compatibility agents for heat transfer fluids include organic phosphates, aromatic esters, aromatic hydrocarbons, esters (butylbenzyl phthalate, for example), and polybutenyl succinic anhydride. Such additives may be used in an amount of about 0.01 to 5 wt. %, preferably about 0.1 to 3 wt. %, and more preferably about 0.5 to 1.5 wt. %.

The heat transfer fluids can include at least one friction modifier. A friction modifier is any material or materials that can alter the coefficient of friction of a surface. Friction modifiers, also known as friction reducers, or lubricity agents or oiliness agents, and other such agents that change the ability of base oils, formulated heat transfer fluids, or functional fluids, to modify the coefficient of friction of a surface may be effectively used in combination with the base oils or heat transfer fluids of the present disclosure if desired. Friction modifiers that lower the coefficient of friction are particularly advantageous in combination with the base oils and heat transfer fluids of this disclosure.

Illustrative friction modifiers may include, for example, organometallic compounds or materials, or mixtures thereof. Illustrative organometallic friction modifiers useful in the heat transfer fluids of this disclosure include, for example, molybdenum amine, molybdenum diamine, an organotungstenate, a molybdenum dithiocarbamate, molybdenum dithiophosphates, molybdenum amine complexes, molybdenum carboxylates, the like, and mixtures thereof. Similar tungsten-based compounds may be preferable.

Other illustrative friction modifiers useful in the heat transfer fluids of this disclosure include, for example, alkoxylated fatty acid esters, alkanolamides, polyol fatty acid esters, borated glycerol fatty acid esters, fatty alcohol ethers, and mixtures thereof.

The heat transfer fluids can include at least one extreme pressure agent (EP). EP agents that are soluble in the oil include sulphur- and chlorosulphur-containing EP agents, chlorinated hydrocarbon EP agents and phosphorus EP agents. Examples of such EP agents include chlorinated wax; sulphurised olefins (such as sulphurised isobutylene), organic sulphides and polysulphides such as dibenzyldisulphide, bis-(chlorobenzyl)disulphide, dibutyl tetrasulphide, sulphurised methyl ester of oleic acid, sulphurised alkylphenol, sulphurised dipentene, sulphurised terpene, and sulphurised Diels-Alder adducts; phosphosulphurised hydrocarbons such as the reaction product of phosphorus sulphide with turpentine or methyl oleate; phosphorus esters such as the dihydrocarbon and trihydrocarbon phosphites, including dibutyl phosphite, diheptyl phosphite, dicyclohexyl phosphite, pentylphenyl phosphite; dipentylphenyl phosphite, tridecyl phosphite, distearyl phosphite and polypropylene substituted phenol phosphite; metal thiocarbamates such as zinc dioctyldithiocarbamate and barium heptylphenol diacid; amine salts of alkyl and dialkylphosphoric acids or derivatives; and mixtures thereof (as described in U.S. Pat. No. 3,197,405, which is incorporated herein by reference).

Extreme pressure agents may be used in an amount of about 0.01 to 5 wt. %, including 0.01 to 1.5 wt. %, 0.01 to 0.2 wt. %, or 0.01 to 0.1 wt. % (on an as-received basis) based on the total weight of the heat transfer fluids.

When heat transfer fluids contain one or more of the additives discussed above, the additive(s) are blended into the heat transfer fluids in an amount sufficient for the heat transfer fluid and the additive to perform an intended function. Typical amounts of such additives useful in the present disclosure are shown in Table 2 below.

It is noted that many of the additives are shipped from the additive manufacturer as a concentrate, containing one or more additives together, with a certain amount of base oil diluent(s). Accordingly, the weight amounts in Table 2 below, as well as other amounts mentioned herein, are directed to the amount of active ingredient (that is the non-diluent portion of the ingredient). The wt. % values indicated below are based on the total weight of the heat transfer fluids.

TABLE 2

| Compound | Approximate Wt. % (Useful) | Approximate Wt. % (Preferred) |
| --- | --- | --- |
| Antioxidant | 0.01-5 | 0.1-1.5 |
| Corrosion Inhibitor | 0.01-5 | 0.1-2 |
| Antifoam Agent | 0-3 | 0.001-0.15 |
| Metal Passivator | 0.01-5 | 0.01-1.5 |
| Pour Point Depressant | 0.01-5 | 0.5-1.5 |
| Seal Compatibility Agent | 0.01-5 | 0.5-1.5 |
| Extreme Pressure Agent | 0.01-5 | 0.01-0.1 |

The foregoing additives are all commercially available materials. These additives may be added independently but also may be precombined in packages which can be obtained from suppliers of heat transfer fluid additives. Additive packages having a variety of ingredients, proportions and characteristics are available and selection of an appropriate package will take the requisite use of the ultimate heat transfer fluid into account.

The heat transfer fluids described herein may be particularly compatible for incorporation in an electric vehicle. Accordingly, electric vehicles disclosed herein may comprise a heat-generating component, and a heat transfer fluid of the present disclosure in contact with the heat-generating component. Any of the heat transfer fluids specified herein may be incorporated in an electric vehicle or a battery system configured for use in an electric vehicle.

The heat transfer fluid may be in contact with an outer surface of the heat-generating component in an electric vehicle, including jacketed and immersed configurations. Jacketed configurations include any configuration in which the heat transfer fluid does not contact the cell components of a battery or other heat-generating component directly. Immersed configurations, in contrast, include any configuration in which one or more cell components of a battery or other heat-generating component are directly contacted by the heat transfer fluid. That is, immersed configurations do not necessarily imply that a battery or other heat-generating component is fully submerged in the heat transfer fluid, although it may be. Certain immersed configurations may include those in which a battery cell is enclosed in a suitable container and the heat transfer fluid circulated between the walls of the container and the battery cell. In more specific embodiments, the heat-generating component may be at least partially immersed in the heat transfer fluid. In some embodiments, the heat-generating component may be fully immersed in the heat transfer fluid. The heat transfer fluid may be in an open or closed system when contacting the outer surface of the heat-generating component. A closed system, for example, may be configured to circulate the heat transfer fluid between the heat-generating component and a heat dissipation structure, such as a heat sink, radiator, or similar structure that is capable of removing excess heat from the heat transfer fluid.

In other embodiments, the heat-generating component may comprise a plurality of interior channels configured for circulating the heat transfer fluid. Thus, the heat transfer fluids may also contact additional surfaces of the heat-generating component other than the outer surface. The engineering design of a particular heat-generating component, such as the electric motor or battery of an electric vehicle, may determine whether interior channels may suitably be present. Emerging electric motor designs, such as electric motors directly mounted to each axle, for example, may require a different cooling approach than those incorporated conventionally within the vehicle's body. When interior channels may be suitably present, the heat transfer fluid may be circulated within the interior channels in addition to contacting the outer surface of the heat-generating component in some embodiments. When a heat transfer fluid contacts the outer surface of the heat-generating component and is also circulated within the interior channels of the heat-generating component, two different sources of the heat transfer fluids may be used. For example, in particular embodiments, the heat transfer fluids contacting the outer surface and circulated within the interior channels may be isolated from one another (e.g., by being present in separate reservoirs), such that the heat transfer fluids do not intermingle. Moreover, the heat transfer fluids contacting the outer surface and circulated within the interior channels may be the same or different, according to various embodiments of the present disclosure.

In some or other embodiments, electric vehicles of the present disclosure may further comprise a heat dissipation structure in fluid communication with the heat transfer fluid. In illustrative embodiments, the heat dissipation structure may comprise a conventional heat sink such as a radiator, heat dissipation fins, or similar air cooling structure. Non-conventional and emerging heat dissipation structures may also be used in various instances. The heat transfer fluid may be configured to circulate between the heat-generating component and the heat dissipation structure in more particular embodiments. Any type of pump may aid in circulating the heat transfer fluid from the heat-generating component to the heat dissipation structure.

In still more particular embodiments, the heat-generating component within the electric vehicles described herein may be a battery, an electric motor, a plurality of electric motors, a power component, a motor component, an axle, or any combination thereof. Power components may include, for example, DC/AC inverters, DC/DC converters, or AC/DC converters. High-power rapid charging stations for electric vehicles may also be cooled using the heat transfer fluids disclosed herein. In some embodiments, the heat transfer fluids described herein may contact at least an outer surface of a battery used in powering the electric vehicle, including immersion or partial immersion of the battery in the heat transfer fluid. The motor or motor components of the electric vehicle may be thermally regulated by a heat transfer fluid of the present disclosure or by conventional heat transfer fluids, such as an aqueous glycol solution. In more particular embodiments, however, both the battery and the motor or motor components of an electric vehicle may be in fluid communication with one or more of the heat transfer fluids described herein. The heat transfer fluid in fluid communication with the battery and the motor or motor components may originate from a common source, or the heat transfer fluids in fluid communication with the battery and with the motor or motor components may originate from different sources. Accordingly, cooling systems suitable for thermally regulating the battery and the electric motor of an electric vehicle may be the same or different in the disclosure herein.

In view of the foregoing, the present disclosure also describes battery systems comprising a heat transfer fluid of the present disclosure in contact with a battery, such as a lithium-ion battery. Battery systems described herein may comprise a battery, and a heat transfer fluid in contact with the battery. Any of the heat transfer fluids specified herein may be used in conjunction with a battery or battery system.

According to particular embodiments of the present disclosure, the heat transfer fluid may be in contact with an outer surface of the battery, including jacketed and immersion configurations. In more specific embodiments, the battery may be at least partially immersed in the heat transfer fluid. In some embodiments, the battery may be fully immersed in the heat transfer fluid, including immersion of the leads of the battery within the heat transfer fluid. The heat transfer fluid contacting an outer surface of the battery may be in an open or closed system. In some or other embodiments, the battery may comprise a plurality of interior channels configured for circulating the heat transfer fluid, such as between the battery and a heat-dissipation structure.

The battery systems disclosed herein may further comprise a heat dissipation structure in fluid communication with the heat transfer fluid, in particular embodiments of the present disclosure. The battery systems may be further configured to circulate the heat transfer fluid between the heat-generating component and a heat dissipation structure in particular embodiments. Suitable heat dissipation structures may include, for example, a heat sink, radiator, or similar structure that is capable of removing excess heat from the heat transfer fluid.

The present disclosure also describes methods for providing thermal regulation of a heat-generating component in some or other embodiments of the present disclosure. Such methods may comprise: providing a heat transfer fluid of the present disclosure, and operating or placing a heat-generating component in contact with the heat transfer fluid, particularly such that a temperature is maintained in a predetermined range. Operation of the heat-generating component may comprise any action that causes the heat-generating component to generate heat. For example, in the case of a battery, charging or discharging the battery may promote excess heat generation, as discussed herein. Thermal management of other heat-generating components such as computer processors within server farms and other high-power electronic components, for example, may also be addressed using the disclosure herein. Rapid charging stations for electric vehicles may also be addressed using the disclosure herein.

The methods may further comprise placing the heat transfer fluid in contact with a surface of the heat-generating component. Particular configurations may include placing the heat transfer fluid in contact with an outer surface of the heat-generating component, including immersion or partial immersion of the heat-generating component in the heat transfer fluid. Jacketed configurations of the heat transfer fluid also reside within the scope of the disclosure herein.

Methods of the present disclosure may further comprise circulating the heat transfer fluid, including, in particular embodiments, circulating the heat transfer fluid between the heat-generating component and a suitable heat dissipation structure.

Embodiments disclosed herein include:

A. Methods for producing methylparaffins. The methods comprise: contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins.

B. Heat transfer fluids comprising methylparaffins. The methylparaffins may be prepared by a method comprising: contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins.

C. Thermal management systems comprising methylparaffins. The thermal management systems comprise a heat transfer fluid comprising methylparaffins, in which the thermal management system is configured to circulate the heat transfer fluid between a heat source and a heat sink. The methylparaffins may be prepared by a method comprising: contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins.

D. Battery systems comprising methylparaffins. The battery systems comprise a battery and a heat transfer fluid comprising methylparaffins in contact with the battery. The methyparaffins may be prepared by a method comprising: contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins.

E. Electric vehicles comprising a battery system comprising methylparaffins. The battery systems comprise a battery and a heat transfer fluid comprising methylparaffins in contact with the battery. The methyparaffins may be prepared by a method comprising: contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins.

F. Thermal management methods using methylparaffins. The methods comprise providing a heat transfer fluid comprising methylparaffins, and operating or placing a heat-generating component in contact with the heat transfer fluid. The methyparaffins may be prepared by a method comprising: contacting at least one linear olefin with hydrogen in the presence of a dual-function supported catalyst comprising a solid acid component and a hydrogenation component, contacting taking place under conditions sufficient to catalytically isomerize the at least one linear olefin into an intermediate product comprising one or more branched olefins; and hydrogenating the one or more branched olefins to form an isoparaffin product comprising one or more methylparaffins.

Embodiments A-F may have one or more of the following additional elements in any combination:

Element 1: wherein the at least one linear olefin comprises at least one linear alpha olefin.

Element 2: wherein the at least one linear olefin comprises a mixture of two or more different linear alpha olefins.

Element 3: wherein the one or more methylparaffins collectively have a branching index ranging from about 1 to about 3.

Element 4: wherein at least a majority of the one or more methylparaffins have one methyl branch.

Element 5: wherein the solid acid component comprises a zeolite, and the hydrogenation component comprises a metal capable of activating molecular hydrogen.

Element 5A: wherein the metal capable of activating molecular hydrogen is Pt, Pd, Ni, W, Co, Mo, or a combination thereof, and an amount of the metal capable of activating molecular hydrogen is about 0.1 wt. % to about 20 wt. % with respect to the zeolite.

Element 6: wherein the zeolite comprises at least one member selected from the group consisting of ZSM-5, ZSM-11, ZSM-12, ZSM-22, ZSM-23, ZSM-35, ZSM-48, zeolite Beta, TON (Theta-1), and any combination thereof.

Element 7: wherein the zeolite comprises ZSM-48 or ZSM-23.

Element 8: wherein the one or more linear olefins have a carbon backbone comprising about 10 to about 26 carbon atoms.

Element 9: wherein each of the one or more methylparaffins has a carbon backbone comprising about 9 to about 25 carbon atoms.

Element 10: wherein the one or more methylparaffins have a carbon backbone comprising at least one carbon atom less than the one or more linear olefins from which the one or more methylparaffins are produced.

Element 11: wherein at least about 70 wt. % of the one or more methylparaffins have a carbon backbone comprising 14 or 15 carbon atoms.

Element 12: wherein the one or more methylparaffins collectively have a pour point of about −15° C. to about −98° C. as measured by ASTM D97.

Element 13: wherein the one or more methylparaffins collectively have a kinematic viscosity at 100° C. of about 0.5 cSt to about 2.5 cSt as measured by ASTM D445.

Element 14: wherein the one or more methylparaffins collectively have a flash point of about 90° C. to about 300° C. as measured by ASTM D92.

Element 15: wherein contacting takes place at a temperature ranging from about 220° C. to about 300° C.

Element 16: wherein contacting takes place at a liquid hourly space velocity of about 1 hr$^{-1}$ to about 4 hr$^{-1}$.

Element 17: wherein the heat transfer fluid is in contact with an outer surface of the battery.

Element 18: wherein the battery is at least partially immersed in the heat transfer fluid.

Element 19: wherein the battery system further comprises a heat dissipation structure in fluid communication with the heat transfer fluid; wherein the battery system is configured to circulate the heat transfer fluid between the battery and the heat dissipation structure.

Element 20: wherein the heat transfer fluid is in contact with an outer surface of the heat-generating component.

Element 21: wherein the heat-generating component is at least partially immersed in the heat transfer fluid.

Element 22: wherein the method further comprises circulating the heat transfer fluid between the heat-generating component and a heat dissipation structure.

Element 23: wherein the heat-generating component is a battery, a power component, a motor, a motor component, or any combination thereof.

Element 24: wherein the battery, the power component, the motor, or the motor component is present in an electric vehicle.

By way of non-limiting example, exemplary combinations applicable to A-F include 1 and 2; 1 and 3; 1-3; 1 and 4; 1, and 5 or 5A; 1, 5 or 5A and 6; 1, 5 or 5A, and 7; 1 and 8; 1 and 9; 1 and 10; 1 and 11; 1 and 12; 1 and 13; 1 and 14; 1 and 15; 1 and 16; 2 and 3; 2 and 4; 2, and 5 or 5A; 2, 5 or 5A, and 6; 2, 5 or 5A, and 7; 2 and 8; 2 and 9; 2 and 10; 2 and 11; 2 and 12; 2 and 13; 2 and 14; 2 and 15; 2 and 16; 4, and 5 or 5A; 4-6, 4, 5 or 5A, and 7; 4 and 8; 4 and 9; 4 and 10; 4 and 11; 4 and 12; 4 and 13; 4 and 14; 4 and 15; 4 and 16; 5 or 5A, and 6; 5 or 5A, and 7; 5 or 5A, and 8; 5 or 5A, and 9; 5 or 5A, and 10; 5 or 5A, and 11; 5 or 5A, and 12; 5 or 5A, and 13; 5 or 5A, and 14; 5 or 5A, and 15; 5 or 5A, and 16; 8 and 9; 8 and 10; 8 and 11; 8 and 12; 8 and 13; 8 and 14; 8 and 15; 8 and 16; 9 and 10; 9 and 11; 9 and 12; 9 and 13; 9 and 14; 9 and 15; 9 and 16; 10 and 11; 10 and 12; 10 and 13; 10 and 14; 10 and 15; 10 and 16; 11 and 15; and 11 and 16. Exemplary combinations applicable to D include any of the foregoing or 1-16 in further combination with one or more of 17, 18 or 19; 17 and 18; 17 and 19; 18 and 19; and 17-19. Exemplary combinations applicable to F include any of the foregoing or 1-16 in further combination with one or more of 20, 21, 22, 23 or 24; 20 and 21; 20 and 22; 20 and 23; 20 and 22-24; 21 and 22; 21-23; 21-24; and 22 and 23.

To facilitate a better understanding of the disclosure herein, the following examples of various representative embodiments are given. In no way should the following examples be read to limit, or to define, the scope of the present disclosure.

EXAMPLES

Alpha Values were determined in accordance with the methods described in U.S. Pat. No. 3,354,078 and in Journal of Catalysis, Vol. 4, p. 527 (1965); Vol. 6, p. 278 (1966) and Vol. 61, p. 395 (1980), each of which is incorporated herein by reference. The experimental conditions used for Alpha Value testing included a constant temperature of 538° C. and a variable flow rate as described in detail in the Journal of Catalysis, Vol. 61, p. 395 (1980).

BET surface areas were measured by nitrogen adsorption/desorption using a Micromeritics Tristar 113020 instrument after degassing of the calcined mesoporous materials for 4 hrs at 350° C. More information regarding the method can be found in, for example, "Characterization of Porous Solids and Powders: Surface Area, Pore Size and Density", S. Lowell et al., Springer, 2004.

Catalyst Preparation

Example 1A: 0.6 Wt. % Pt-Coated H-Form ZSM-48. High-activity small ZSM-48 crystals with a silica:alumina molar ratio of ~70:1 were synthesized as described in U.S. Pat. No. 7,482,300, which is incorporated herein by reference. The XRD pattern of the as-synthesized zeolite material showed a typical topology pattern for a pure phase of ZSM-48, and the SEM showed agglomerates of small crystals. The as-synthesized crystals were dried and calcined in nitrogen for ~3 hours at ~1000° F., and then ammonium exchanged with ~1N ammonium nitrate solution. Following exchange, the crystals were calcined in air for ~6 hours at ~1000° F. The resulting ZSM-48 crystals had an Alpha value of ~100, exhibited a hexane sorption of 47 mg/g, and had a BET surface area of 296 m$^2$/g. The air-calcined material was then impregnated with platinum (0.6 wt. % Pt loading) via incipient wetness using tetraammineplatinum nitrate followed by drying at 250° F. (120° C.) and calcining in full air at 680° F. (360° C.) for 3 hours.

Example 1B: 0.6 Wt. % Pt-Coated H-Form ZSM-23. High activity small ZSM-23 crystals with a silica:alumina molar ratio of ~40/1 were synthesized as described in U.S. Pat. No. 8,500,991, which is incorporated herein by reference. The XRD pattern of the as-synthesized zeolite material a typical topology pattern for ZSM-23, and the SEM showed agglomerates of small crystals. The as-synthesized crystals were converted into the hydrogen form by three ion exchanges with ammonium nitrate solution at room temperature, followed by drying at 250° F. (120° C.) and calcining at 1000° F. (540° C.) for 6 hours. The resulting ZSM-23 crystals had an Alpha value of ~520, exhibited a hexane sorption of ~50 mg/g, and had a surface area of 287 m$^2$/g. The air-calcined material was then impregnated with platinum (0.6 wt. % Pt loading) via incipient wetness using tetraammineplatinum nitrate followed by drying at 250° F. (120° C.) and calcining in full air at 680° F. (360° C.) for 3 hours.

Isomerization Reactions

General Procedure. A reactor containing a dry catalyst bed was first heated to 150° C. at a 10° C./min ramp rate under 250 sccm N$_2$ at ambient pressure for 0.5 hours. The flow was then switched to H$_2$ at 250 sccm, and the temperature was ramped to 300° C. and maintained at this level for 3 hours at ambient pressure. The temperature was then reduced to 150° C. After reaching the desired temperature, the hydrogen flow and the pressure were changed to the desired level specified in the specific examples below, with the liquid flow rate of the feed initially set at 2 h$^{-1}$. Once the feed reached the product knock out, the liquid flow rate was changed to the desired liquid flow rate specified in the examples below, and the temperature was ramped to the desired reaction temperature at 10° C./min. Measurement of the reaction time began once the desired reaction temperature was reached. Material produced over the first 6 hours was discarded. Afterward, the reaction product was collected twice a day and analyzed by GC.

Example 2A: A 1-hexadecene feed was exposed to the catalyst of Example 1A at 260° C. at a liquid hourly space velocity of 2 h$^{-1}$ and a pressure of 250 psi. The H$_2$ flow was 250 sccm. The product distribution was subsequently analyzed by gas chromatography.

Example 2B: Example 2A was repeated, except the catalyst of Example 1B was used.

Figure 1:
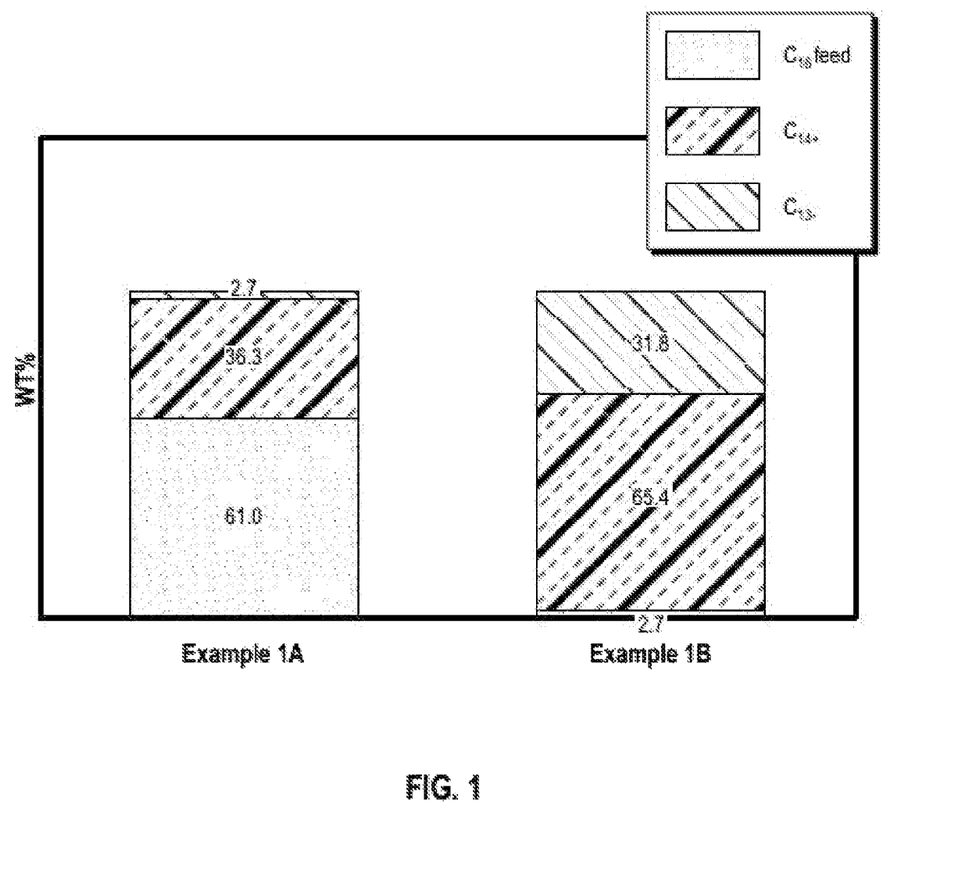
FIG. 1 shows a bar graph illustrating the product distribution obtained when treating 1-hexadecene with various supported catalysts comprising a solid acid component and a hydrogenation component in the presence of hydrogen.

FIG. 1 shows a bar graph illustrating the product distribution obtained when treating 1-hexadecene with various dual-function supported catalysts comprising a solid acid component and a hydrogenation component in the presence of hydrogen. As shown, under the initial testing conditions with Pt-coated ZSM-48 (Catalyst of Example 1A), 36.3 wt. % of the LAO feed was converted into $C_{14+}$ products, and 61 wt. % of the LAO feed was unchanged. A minimal amount of more extensive cracking to unwanted $C_{13-}$ products (2.7 wt. %) occurred. Pt-Coated ZSM-23 (Catalyst of Example 1B), in contrast, under the initial testing conditions, led to more complete conversion of the feed, with both $C_{14+}$ products (65.4 wt. %) and unwanted $C_{13-}$ products (31.8 wt. %) being formed more extensively than with Pt-coated ZSM-48 (Catalyst of Example 1A).

Example 3A. Example 2A was repeated, except varying the reaction parameters as specified in Table 3 below.

TABLE 3

0.6 Wt. % Pt-Coated H-Form ZSM-48
(Catalyst of Example 1A) Conditions Used

| Variable | Example 2A | A | B | C | D | E | F | G | H |
|---|---|---|---|---|---|---|---|---|---|
| Temperature (° C.) | 260 | 260 | 260 | 260 | 260 | 260 | 260 | 280 | 290 |
| H$_2$ Flow (sccm) | 250 | 200 | 150 | 100 | 100 | 50 | 50 | 50 | 50 |
| Pressure (psig) | 200 | 200 | 200 | 200 | 100 | 100 | 100 | 100 | 100 |
| LHSV (h$^{-1}$) | 2 | 2 | 2 | 2 | 2 | 2 | 3 | 3 | 3 |

Figure 2:
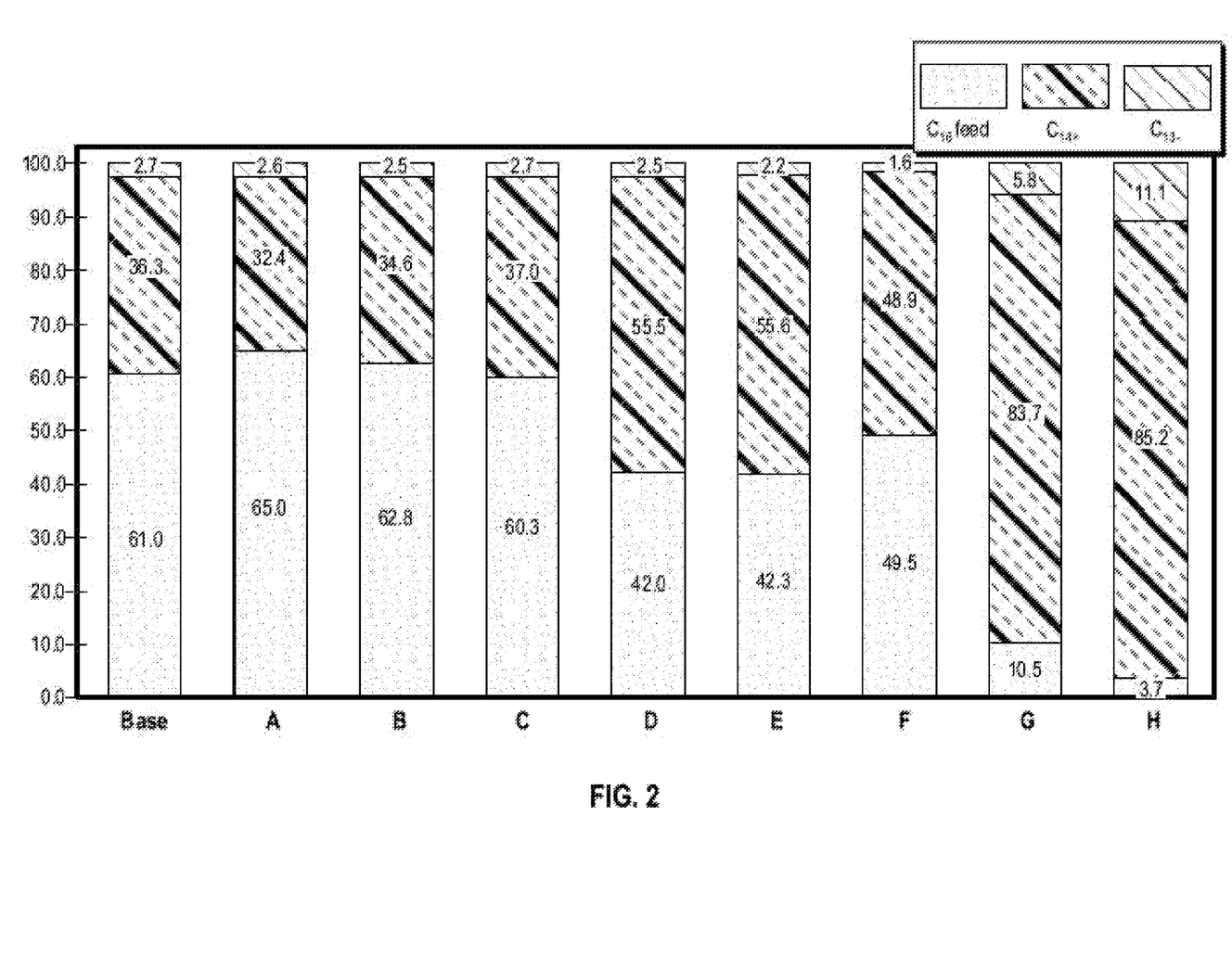
FIG. 2 shows a bar graph illustrating the product distribution obtained when treating 1-hexadecene with 0.6 wt. % Pt-coated ZSM-48 in the presence of hydrogen under various conditions.

FIG. 2 shows a bar graph illustrating the product distribution obtained when treating 1-hexadecene with the catalyst of Example 1A in the presence of hydrogen under various conditions, as specified in Table 3 above. As shown, the conversion of the 1-hexadecene feed increased considerably under conditions G and H, leading to formation of desired $C_{14+}$ products at greater than 80 wt. %, accompanied by only a minimal increase in undesired $C_{13-}$ products.

Example 3B. Example 2B was repeated, except varying the reaction parameters as specified in Table 4 below.

TABLE 4

0.6 Wt. % Pt-Coated H-Form ZSM-23
(Catalyst of Example 1B) Conditions Used

| Variable | Example 1B | A | B | C | D | E | F | G | H |
|---|---|---|---|---|---|---|---|---|---|
| Temperature (° C.) | 260 | 240 | 240 | 240 | 240 | 245 | 245 | 250 | 250 |
| H$_2$ Flow (sccm) | 250 | 250 | 150 | 100 | 100 | 100 | 100 | 100 | 100 |
| Pressure (psig) | 200 | 200 | 200 | 200 | 100 | 100 | 100 | 200 | 200 |
| LHSV (h$^{-1}$) | 2 | 2 | 2 | 2 | 2 | 2 | 3 | 2 | 3 |

Figure 3:
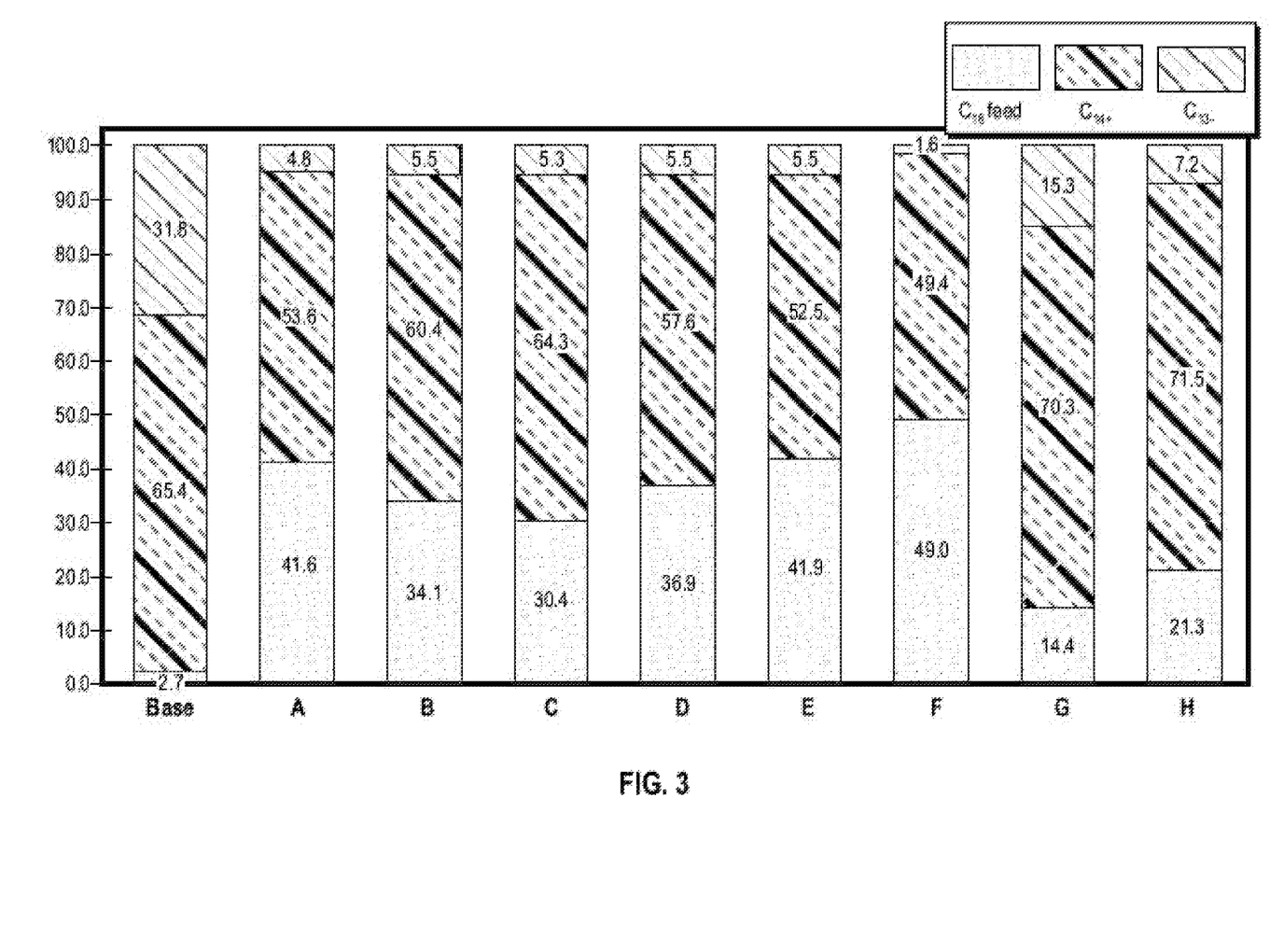
FIG. 3 shows a bar graph illustrating the product distribution obtained when treating 1-hexadecene with 0.6 wt. % Pt-coated ZSM-23 in the presence of hydrogen under various conditions.

FIG. 3 shows a bar graph illustrating the product distribution obtained when treating 1-hexadecene with the catalyst of Example 1B in the presence of hydrogen under various conditions, as specified in Table 4 above. As shown, the formation of undesired $C_{13-}$ products decreased considerably under conditions A-F. Under conditions G and H, good conversion of the 1-hexadecene feed was still realized while leading to formation of desired $C_{14+}$ products at greater than 70 wt. %, accompanied by only a small increase in undesired $C_{13-}$ products.

As shown in Examples 3A and 3B, various reaction parameters, as well as the catalyst, may be adjusted to drive conversion of the LAO feed to a desired product size range. For example, in the case of the more active catalyst ZSM-23 (catalyst of Example 1B), lower temperatures and higher pressures may be more favorable for producing desired $C_{14+}$ products as compared to ZSM-48 (catalyst of Example 1A).

Example 4: The catalyst of Example 1A was used for processing several LAO feeds under varying reaction conditions to determine the impact on physical properties of the methylparaffins obtained. The reaction product was briefly heated at 165° C. under vacuum (<3 torr) to remove light material ($\leq C_{10}$ material) prior to conducting physical property measurements. Reaction conditions and physical property data are specified in Table 5 below.

TABLE 5

| Entry | Feed | Temp. (° C.) | LHSV (h⁻¹) | Liq. Flow Rate (mL/h) | H₂ Flow Rate (sccm) | Press. (psig) | Pour Point ASTM D97 (° C.) | Open Cup Flash Point ASTM D92 (° C.) | KV100 ASTM D445 (cSt) |
|---|---|---|---|---|---|---|---|---|---|
| 1 | 1-octadecene | 290 | 3 | 3.9 | 50 | 100 | −51 | 136 | 1.404 |
| 2 | 3:2 1-hexadecene + 1-octadecene | 265 | 3 | 3.9 | 50 | 100 | −30 | 140 | 1.265 |
| 3 | 3:2 1-hexadecene + 1-octadecene | 265 | 3 | 3.9 | 18 | 100 | −15 | 140 | 1.290 |

As shown, choice of the feed and the reaction conditions used led to considerably different physical properties of the resulting methylparaffins.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed, including the lower limit and upper limit. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is the following:

1. A method comprising:
    contacting at least one linear olefin with hydrogen in the presence of a dual-function supported catalyst comprising a solid acid component and a hydrogenation component, wherein the at least one linear olefin comprises hexadecene and wherein the solid acid component of the dual-function supported catalyst comprises ZSM-48, the contacting taking place under at a temperature ranging from about 280° C. to about 300° C. at a liquid hourly space velocity (LHSV) ranging from about 2 h$^{-1}$ to about 3 h$^{-1}$ to catalytically isomerize the at least one linear olefin into an intermediate product comprising one or more branched olefins; and hydrogenating the one or more branched olefins to form an isoparaffin product comprising one or more methylparaffins, wherein the one or more methylparaffins have a branching index ranging from about 1 to about 3, and at least a majority of the one or more methylparaffins have one branch.

2. The method of claim 1, wherein the at least one linear olefin comprises a mixture of two or more different linear alpha olefins.

3. The method of claim 1, wherein the solid acid component comprises a zeolite, and the hydrogenation component comprises a metal capable of activating molecular hydrogen.

4. The method of claim 3, wherein the zeolite comprises at least one member selected from the group consisting of ZSM-5, ZSM-11, ZSM-12, ZSM-22, ZSM-23, ZSM-35, ZSM-48, zeolite Beta, TON (Theta-1), and any combination thereof.

5. The method of claim 4, wherein the metal capable of activating molecular hydrogen is Pt, Pd, Ni, W, Co, Mo, or a combination thereof, and an amount of the metal capable of activating molecular hydrogen is about 0.1 wt. % to about 20 wt. % with respect to the zeolite.

6. The method of claim 1, wherein the one or more linear olefins have a carbon backbone comprising about 10 to about 26 carbon atoms.

7. The method of claim 1, wherein each of the one or more methylparaffins has a carbon backbone comprising about 9 to about 25 carbon atoms.

8. The method of claim 1, wherein the one or more methylparaffins have a carbon backbone comprising at least one carbon atom less than the one or more linear olefins from which the one or more methylparaffins are produced.

9. The method of claim 1, wherein at least about 70 wt. % of the one or more methylparaffins have a carbon backbone comprising 14 or 15 carbon atoms.

10. The method of claim 1, wherein the one or more methylparaffins collectively have a pour point of about −15° C. to about −98° C. as measured by ASTM D97.

11. The method of claim 1, wherein the one or more methylparaffins collectively have a kinematic viscosity at 100° C. of about 0.5 cSt to about 2.5 cSt as measured by ASTM D445.

12. The method of claim 1, wherein the one or more methylparaffins collectively have a flash point of about 90° C. to about 300° C. as measured by ASTM D92.

13. A heat transfer fluid prepared by the method of claim 1.

14. A thermal management system comprising the heat transfer fluid of claim 13, the thermal management system being configured to circulate the heat transfer fluid between a heat source and a heat dissipation structure.

15. A battery system comprising:
a battery; and
the heat transfer fluid of claim 13 in contact with the battery.

16. The battery system of claim 15, wherein the heat transfer fluid is in contact with an outer surface of the battery.

17. The battery system of claim 15, wherein the battery is at least partially immersed in the heat transfer fluid.

18. The battery system of claim 15, further comprising:
a heat dissipation structure in fluid communication with the heat transfer fluid;
wherein the battery system is configured to circulate the heat transfer fluid between the battery and the heat dissipation structure.

19. An electric vehicle comprising the battery system of claim 15.

20. A method comprising:
providing the heat transfer fluid of claim 13; and
operating or placing a heat-generating component in contact with the heat transfer fluid.

21. The method of claim 20, wherein the heat transfer fluid is in contact with an outer surface of the heat-generating component.

22. The method of claim 20, wherein the heat-generating component is at least partially immersed in the heat transfer fluid.

23. The method of claim 20, further comprising:
circulating the heat transfer fluid between the heat-generating component and a heat dissipation structure.

24. The method of claim 20, wherein the heat-generating component is a battery, a power component, a motor, a motor component, or any combination thereof.

25. The method of claim 24, wherein the battery, the power component, the motor, or the motor component is present in an electric vehicle.

26. A method comprising:
contacting at least one linear olefin with hydrogen in the presence of a dual-function supported catalyst comprising a solid acid component and a hydrogenation component, wherein the at least one linear olefin comprises hexadecene and wherein the solid acid component of the dual-function supported catalyst comprises ZSM-23, the contacting taking place under at a temperature ranging from about 240° C. to about 260° C. at a liquid hourly space velocity (LHSV) ranging from about 2 h$^{-1}$ to about 3 h$^{-1}$ to catalytically isomerize the at least one linear olefin into an intermediate product comprising one or more branched olefins; and hydrogenating the one or more branched olefins to form an isoparaffin product comprising one or more methylparaffins, wherein the one or more methylparaffins have a branching index ranging from about 1 to about 3, and at least a majority of the one or more methylparaffins have one branch.

27. The method of claim 26, wherein at least about 70 wt. % of the one or more methylparaffins have a carbon backbone comprising 14 or 15 carbon atoms.

28. The method of claim 26, wherein the one or more methylparaffins have a carbon backbone comprising at least one carbon atom less than the one or more linear olefins from which the one or more methylparaffins are produced.

* * * * *